(12) United States Patent
Lacome

(10) Patent No.: US 8,423,327 B2
(45) Date of Patent: Apr. 16, 2013

(54) METHODS AND SYSTEMS OF ENGINEERING ANALYSIS USING A HYBRID APPROACH WITH FEM AND ADAPTIVE SPH

(75) Inventor: Jean Luc Lacome, Grenade sur Garonne (FR)

(73) Assignee: Livermore Software Technology Corporation, Livermore, CA (US)

( * ) Notice: Subject to any disclaimer, the term of this patent is extended or adjusted under 35 U.S.C. 154(b) by 1101 days.

(21) Appl. No.: 12/042,385

(22) Filed: Mar. 5, 2008

(65) Prior Publication Data

US 2009/0228246 A1 Sep. 10, 2009

(51) Int. Cl.
*G06F 7/60* (2006.01)
*G06F 17/10* (2006.01)

(52) U.S. Cl.
USPC .......................................................... 703/2

(58) Field of Classification Search ................... 703/1, 2
See application file for complete search history.

(56) References Cited

U.S. PATENT DOCUMENTS

2007/0038424 A1* 2/2007 Schirm et al. ..................... 703/9

OTHER PUBLICATIONS

Vuyst et al, "Coupling between meshless and finite element methods", Jun. 2004, International Journal of Impact Engineering 31 (2005), pp. 1054-1064.*
Fernandez-Mendez et al, "Continuous blending of SPH with finite elements", Mar. 2005, Computers and Structures 83 (2005), pp. 1448-1458.*
Faraud et al, "SPH Simulations of Debris Impacts Using Two Different Computer Codes", 1999, International Journal of Impact Engineering 23 (1999), pp. 249-260.*
Groenenboom, "Numerical Simulation of 2D and 3D Hypervelocity Impact Using the SPH Option in PAM-SHOCK", 1997, International Journal Impact Engineering 20, pp. 309-323.*
Plimpton et al, "Parallel Transient Dynamics Simulations: Algorithms for Contact Detection and Smoothed Particle Hydrodynamics", 1988, Journal of Parallel and Distributed Computing 50, pp. 104-122.*
Johnson et al. "An algorithm to automatically convert distored finite elements into meshless particles during dynamic deformation", Apr. 2002, International Journal of Impact Engineering, 27, pp. 997-1013.*
Johnson et al. "Conversion of 3D distorted elements into meshless particles during dynamic deformation", Jan. 2003, International Journal of Impact Engineering, 28, pp. 947-966.*

* cited by examiner

*Primary Examiner* — Dwin M Craig
(74) *Attorney, Agent, or Firm* — Roger H. Chu

(57) ABSTRACT

Systems and methods of computer aided engineering analysis using hybrid approach of finite element method (FEM) and adaptive smoothed particle hydrodynamics (SPH) are described. According to one aspect, a computer-aided engineering analysis is performed to simulate an impact event between structures. A FEM grid model is created to represent the structures using a plurality of solid elements which represents geometry and material properties. Once a contact between two structures resulted into a material or structural failure according to predefined material constitutive equation, solid elements representing the failed portion of the structure are removed. Each failed solid element is then replaced by a plurality of particles to be analyzed using the SPH analysis. The particles replacing the failed element inherit all of the states and properties of the failed element, such as location, mass, velocity, acceleration, etc. The replacement is conducted according to the principles of mass, momentum and energy conservation.

15 Claims, 14 Drawing Sheets

300

$T=T_1$

140

$T=T_2$

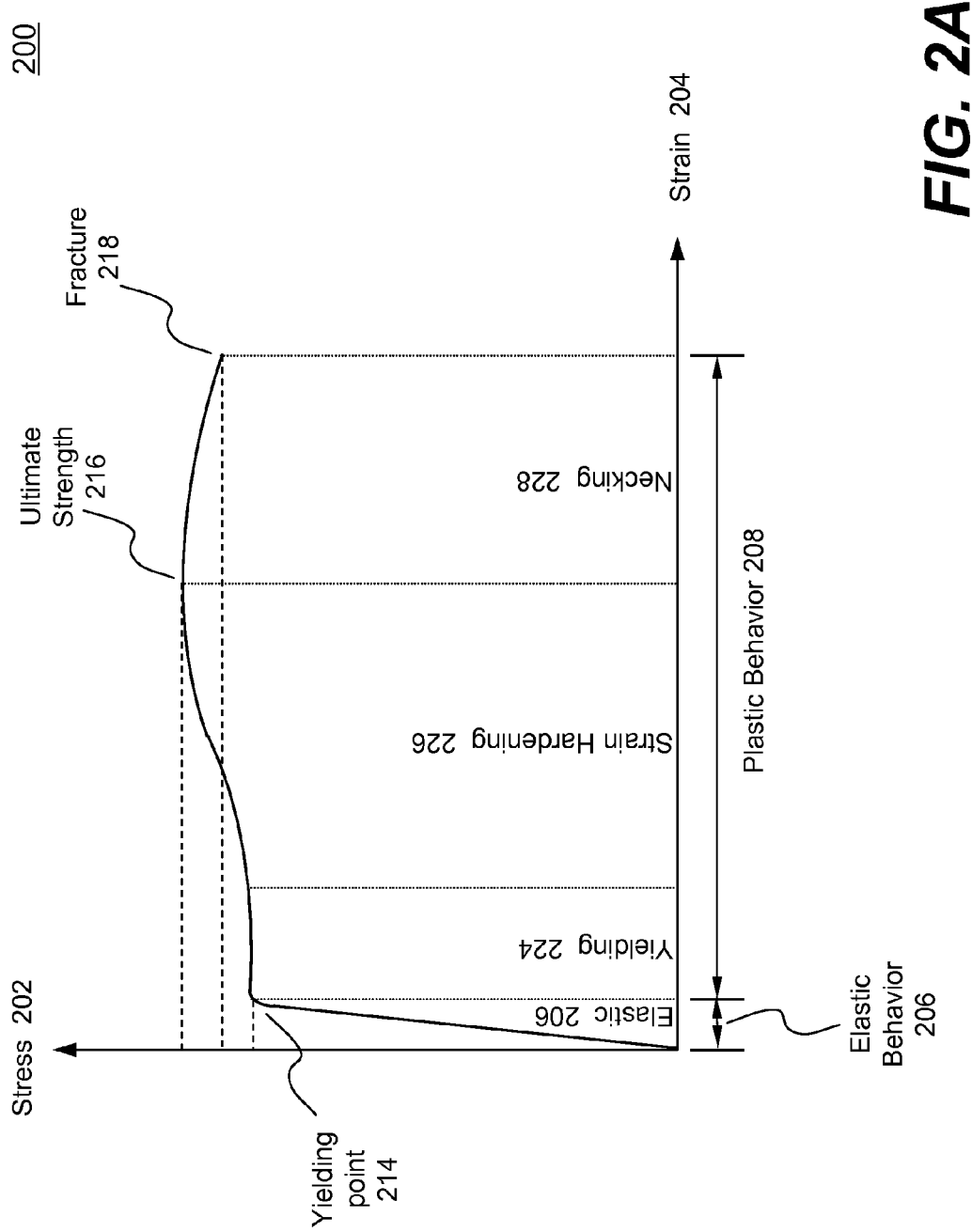

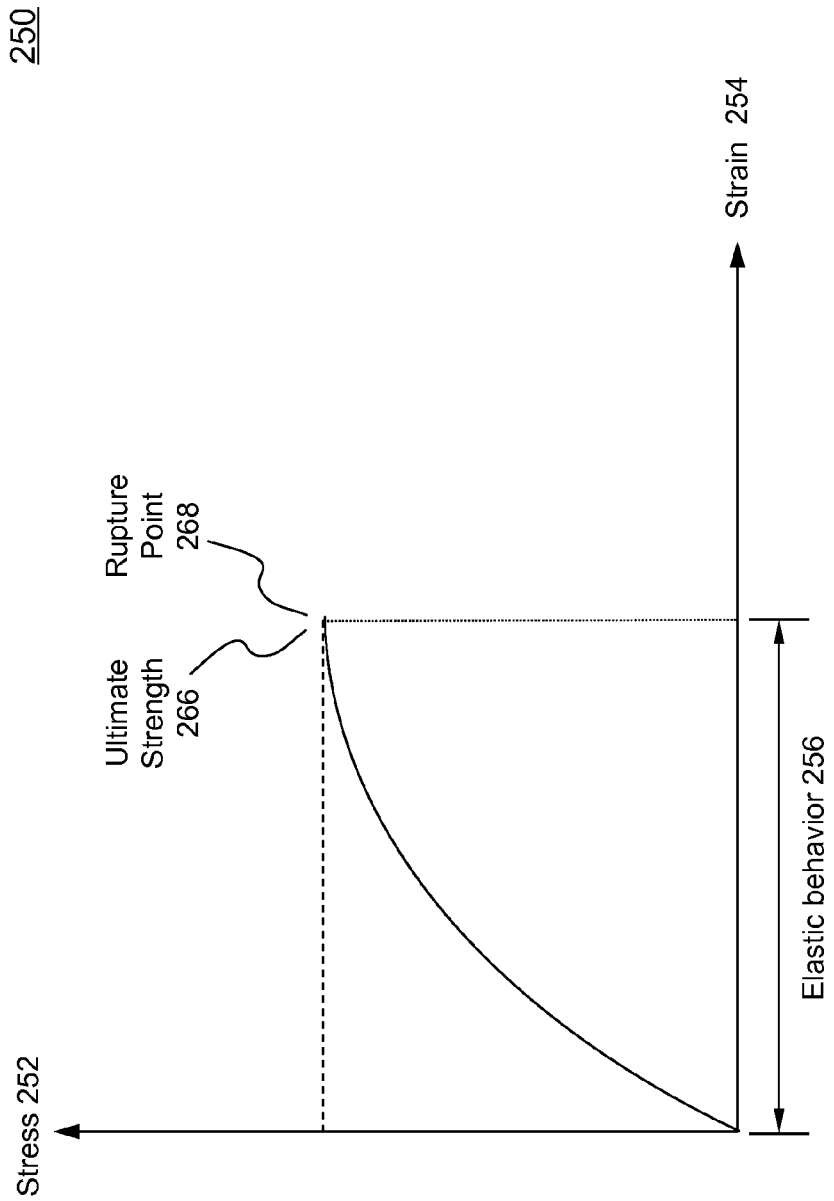

METHODS AND SYSTEMS OF ENGINEERING ANALYSIS USING A HYBRID APPROACH WITH FEM AND ADAPTIVE SPH

FIELD OF THE INVENTION

The present invention generally relates to computer aided engineering analysis, more particularly to methods and systems of engineering analysis using a hybrid approach including finite element method (FEM) and adaptive smoothed particle hydrodynamics (SPH).

BACKGROUND OF THE INVENTION

Continuum mechanics has been used for simulating continuous matter such as solids and fluids (i.e., liquids and gases). Differential equations are employed in solving problems in continuum mechanics. Many numerical procedures have been used. One of the most popular methods is finite element analysis (FEA), which is a computerized method widely used in industry to model and solve engineering problems relating to complex systems such as three-dimensional non-linear structural design and analysis. FEA derives its name from the manner in which the geometry of the object under consideration is specified. With the advent of the modern digital computer, FEA has been implemented as FEA software. Basically, the FEA software is provided with a grid-based model of the geometric description and the associated material properties at each point within the model. In this model, the geometry of the system under analysis is represented by solids, shells and beams of various sizes, which are called elements. The vertices of the elements are referred to as nodes. The model is comprised of a finite number of elements, which are assigned a material name to associate with material properties. The model thus represents the physical space occupied by the object under analysis along with its immediate surroundings. The FEA software then refers to a table in which the properties (e.g., stress-strain constitutive equation, Young's modulus, Poisson's ratio, thermo-conductivity) of each material type are tabulated. Additionally, the conditions at the boundary of the object (i.e., loadings, physical constraints, etc.) are specified. In this fashion a model of the object and its environment is created.

Once the model is defined, FEA software can perform a simulation of the physical behavior under the specified loading or initial conditions. FEA software is used extensively in the automotive industry to simulate front and side impacts of automobiles, occupant dummies interacting with airbags, and the forming of body parts from sheet metal. Such simulations provide valuable insight to engineers who are able to improve the safety of automobiles and to bring new models to the market more quickly. The simulation is generally performed in time domain meaning the FEA is computed at many solution cycles starting from an initial solution cycle, at each subsequent solution cycle, the simulation time is incremented by a time step referred to as $\Delta T$.

Solid elements are typically used for modeling thick parts or solid bodies. In three dimensions, a solid element can be shaped like brick or hexahedron. The lowest order brick element has a node at each corner and is thus called the 8-node brick or hexahedral element. The compatible stress and strain fields have linear terms within the element domain. There are other types of solid elements such the 6-node pentahedral element.

One of the most challenging FEA tasks is to simulate an impact event involving structural fracture. As the modern computer improves, engineers not only wish to simulate the behavior in an impact event with structural failure or fracture, they also want to simulate debris resulting from the impact. However, the debris is not suitable with by solving a continuum mechanics problem using a FEA.

Another problem in FEA is the adaptivity. In order to get more accurate simulation, it is preferable to refine the FEM grid model around the region of interest (e.g., contact region in an impact event). However, the adaptivity is not very easy performed in the FEA.

Given the foregoing drawbacks, problems and limitations of the prior art, it would be desirable to have improved methods and systems to perform engineering analysis that can simulate an impact event with structural failure or fracture including the resulting debris.

BRIEF SUMMARY OF THE INVENTION

This section is for the purpose of summarizing some aspects of the present invention and to briefly introduce some preferred embodiments. Simplifications or omissions in this section as well as in the abstract and the title herein may be made to avoid obscuring the purpose of the section. Such simplifications or omissions are not intended to limit the scope of the present invention.

The present invention discloses systems and methods of computer aided engineering analysis using hybrid approach of finite element method (FEM) and adaptive smoothed particle hydrodynamics (SPH). According to one aspect of the present invention, a computer aided engineering analysis is performed to simulate an impact event between two or more objects (e.g., structures). A FEM model (i.e., grid-based model) is created to represent the structures using a plurality of solid elements which represents geometry and material properties. Once a contact between two structures due to the impact event resulted into a material or structural failure according to predefined material constitutive equation, solid elements representing the failed portion of the structure are removed. Each failed solid element is then replaced by a plurality of particles to be analyzed using the SPH analysis. The particles replacing the failed element inherit all of the states and properties of the failed element, such as location, mass, velocity, acceleration, etc. The replacement is conducted according to the principles of mass, momentum and energy conservation. There are a number of adaptive SPH partitioning schemes to convert each of the failed elements into a plurality or particles, for example, one to two, one to four, one to six, one to eight or more.

According to another aspect, an SPH analysis is performed for a group of particles resulted from a conversion from failed solid elements in the FEM analysis. SPH analysis is a computational method used for simulating fluid flows. However SPH has been used in many fields such as astrophysics, ballistics, vulcanology and tsunami. SPH works by dividing or partitioning the field (e.g., fluid, structure, etc.) into a group of particles. Each of the particles includes a spatial distance referred to as "smoothed length", which determines a domain of influence (e.g., a circular area with a radius of "smoothed length"). A kernel function is computed for all of the particles within the domain of influence. Adaptivity can be achieved with relative ease in SPH because there is no grid or mesh constraint.

According to one embodiment, the present invention is method of engineering analysis using a hybrid approach of finite element method (FEM) and adaptive smoothed particle hydrodynamics (SPH), the method comprises at least the following: (a) defining a FEM grid model representing a plurality of structures in an impact event, the FEM grid model includes a plurality of solid elements; (b) defining a group of first particles representing debris resulting from the impact event, the group of first particles is empty at onset; (c) starting a time domain simulation of the engineering analysis of the impact event using the FEM in an initial solution cycle; (d) determining whether there has been at least one solid element failed in the FEM according to a set of structural failure criteria; (e) converting each of the at least one failed solid element into a plurality of second particles, which inherits states of said each of the at least one failed solid element and merging the plurality of second particles into the group of first particles if required; (f) incrementing time in the time domain simulation to a next solution cycle; (g) performing the engineering analysis of the non-empty group of first particles using the adaptive SPH and performing the engineering analysis of the FEM grid model with remaining elements using the FEM in the next solution cycle; and (h) repeating (d)-(g) until the time domain simulation ends.

The method further comprises partitioning said each of the at least one failed solid element to a plurality of portions in accordance with an adaptivity rule, wherein each of the plurality of second particles corresponds to respective one of the plurality of portions and maintaining conservation of mass, moment and energy between said each of the at least one failed solid element and the plurality of second particles.

One of the objects, features, and advantages of the present invention is to allow a more realistic time domain simulation of engineering analysis of an impact event resulted into debris. Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

FIGS. 2A-2B are diagrams illustrating two exemplary stress-strain curves may be used as failure criteria in accordance with one embodiment of the present invention;

DETAILED DESCRIPTION

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the present invention are discussed herein with reference to FIGS. 1A-6. However, those skilled in the art will readily appreciate that the detailed description given herein with respect to these figures is for explanatory purposes as the invention extends beyond these limited embodiments.

Figure 1A:
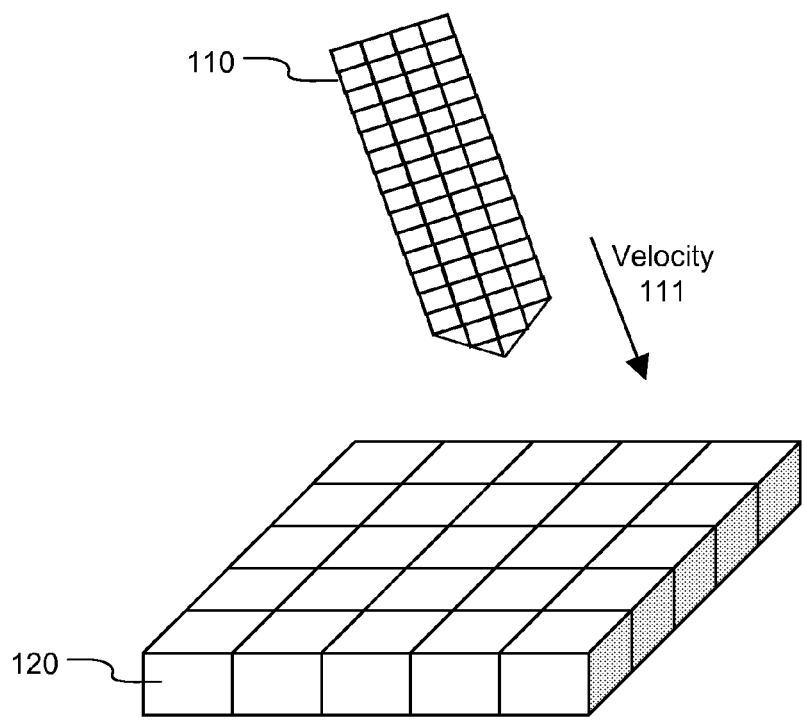
FIGS. 1A-1C are a series of diagrams showing an impact event between a projectile and a structure with flat surface.
Figure 1B:
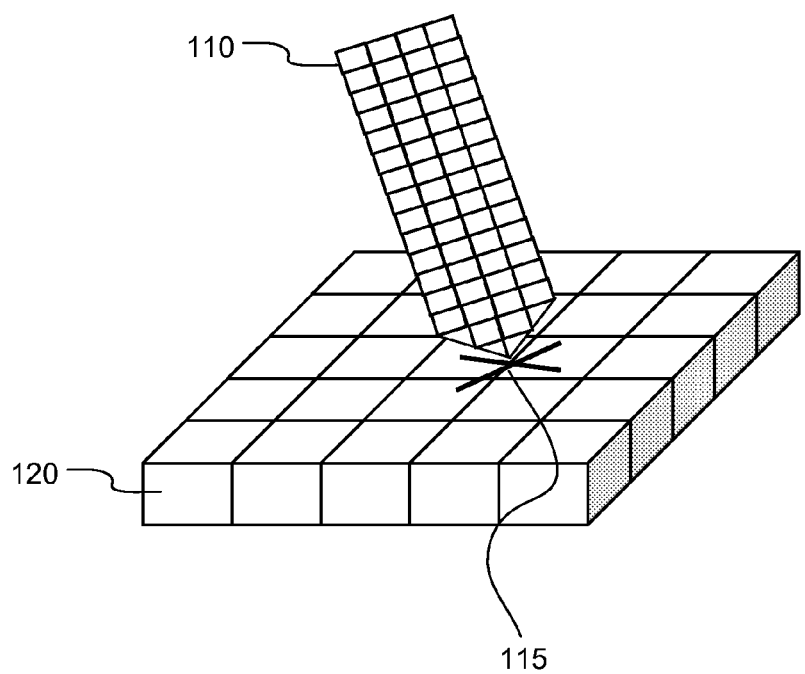
Figure 1C:
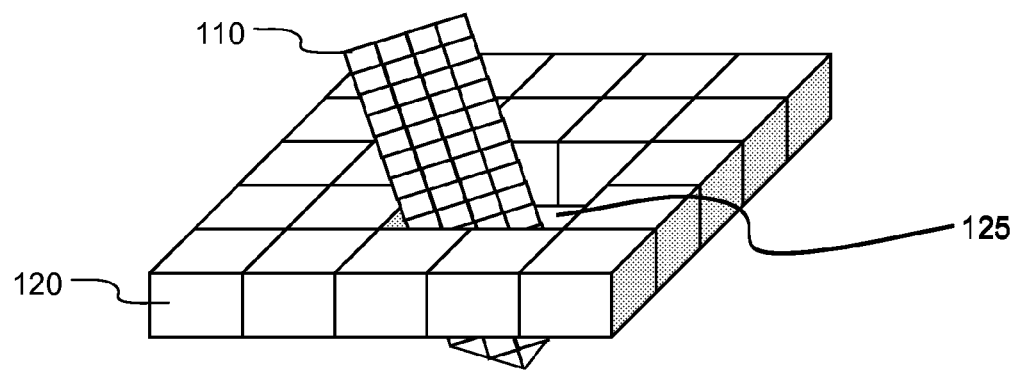

FIGS. 1A-1C show a sequence of an exemplary impact event between a projectile 110 and a structure 120 with a flat surface. The projectile 110 has a mass and a velocity 111 initially shown at time $T_0$ in FIG. 6. The projectile 110 travels towards the structure 120, which has its own material property (e.g., steel, concrete, etc.). The projectile 110 and the structure 120 are represented by finite element method (FEM) grid models. For illustration simplicity, the FEM model for the projectile 110 is shown as a two-dimensional, while the structure 120 as three-dimensional. In reality, both models are three-dimensional and may be created with different number of solid elements (e.g., hexahedral elements). Next, shown in FIG. 1B, the projectile 110 makes an initial contact with the structure 120 at location 115 on the flat surface after a later time $T_1$ from the initial position. Finally, at time $T_2$, the projectile 110 has penetrated the structure 120 shown in FIG. 1C. Impact area 125 with solid elements removed represents structural failure of the structure 120 due to the impact from the projectile 110. The exemplary impact event as shown and described herein may be simulated by a computer-implemented method in accordance with one embodiment of the present invention. The benefit is to predict the structural behavior of the impact event without actually performing a physical test, which is not only costly, but very difficult to perform accurately.

Structural failure has been studied by engineers and material scientists for many years. One method to classify the material behavior is to conduct a tension test of material sample, for example, an elongated cylindrical specimen. The tension is applied along the longitudinal axis of the specimen. The result of such test is a stress-strain curve showing the relationship between stress, derived from measuring the load applied on the sample, and strain, derived from the deformation of the sample, for example, elongation. The test may also be formed with other loading such as compression and torsion.

FIG. 2A and FIG. 2B show exemplary first 200 and second 250 stress-strain curves, which may be used for determining material failure in a structure, according to one embodiment of the present invention. The first stress-strain curve 200 is for a ductile material such as steel. The first curve 200 has a vertical axis representing stress 202 and a horizontal axis strain 204. The material has two behaviors: elastic region 206 and plastic region 208. The plastic region 208 is further divided into three categories: yielding 224, strain hardening 226 and necking 228. At the top end of the elastic region of the first curve 200 is a yielding point 214, to which the yielding stress corresponds. The ultimate stress corresponds to the ultimate strength point 216, while the fracture or failure stress to the fracture location 218. According to one aspect of the present invention, a material is considered a failed material (i.e., failed structure) when the material has experienced the fracture stress with a numerical calculation in a simulation of engineering analysis.

The second stress-strain curve 250 shows a very different material behavior comparing to that of the first curve 200. Typical material behavior shown in the second curve 250 is hyperelastic material such as rubber or foam. Such material may only have elastic region 256 and the ultimate strength 266 and rupture point 268 may be the same. Since the material properties can be represented by a numerical relationship between stress 202 an strain 204, such relationship is defined as constitutive equation in a computer implemented method that may be used by one embodiment of the present invention. For example, once a structural failure has determined during a time domain simulation using FEM, elements representing the failed structure are removed.

Figure 3A:
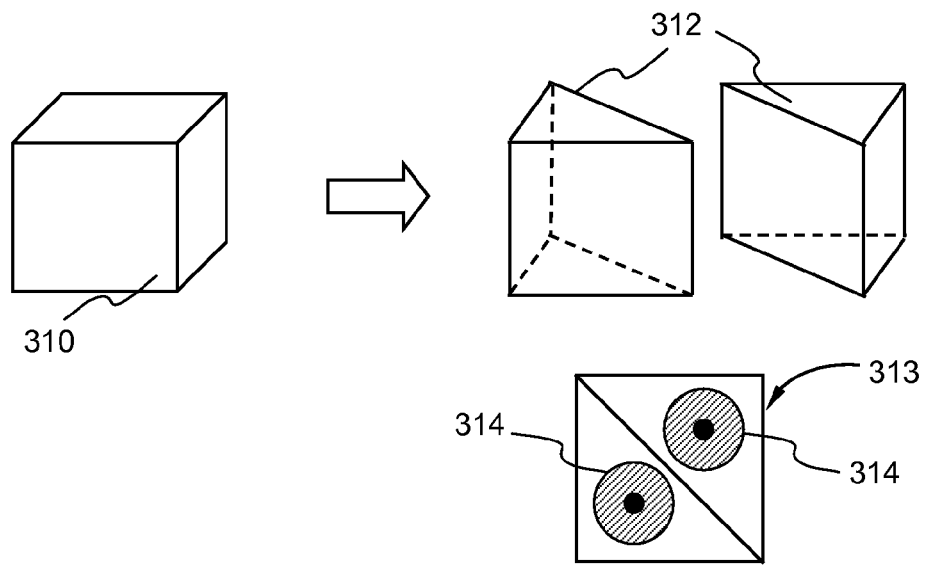
FIGS. 3A-3G are several diagrams showing various exemplary means for converting an failed element into a plurality of particles in accordance with one embodiment of the present invention.

According to one aspect of the present invention, debris resulted from the impact (i.e., removed elements) is represented by particles to be calculated by smoothed particle hydrodynamics (SPH). FIGS. 3A-3G show various exemplary schemes to partition a failed hexahedral element 310 (i.e., 8-node solid) in accordance with one embodiment of the present invention. In FIG. 3A, the failed element 310 is divided diagonally into two prisms 312. Each of the two prisms 312 is converted into two particles 314 shown in a plan view 313. The particles 314 inherit states of the failed element 310, for example, location, mass, momentum and energy. There may be a number of ways to select locations including, but limited to, center of mass, gravity, geometry, integration point. In other words, principles of conservation of mass, momentum and energy are preserved when converting each failed element into a plurality of particles.

Figure 3B:
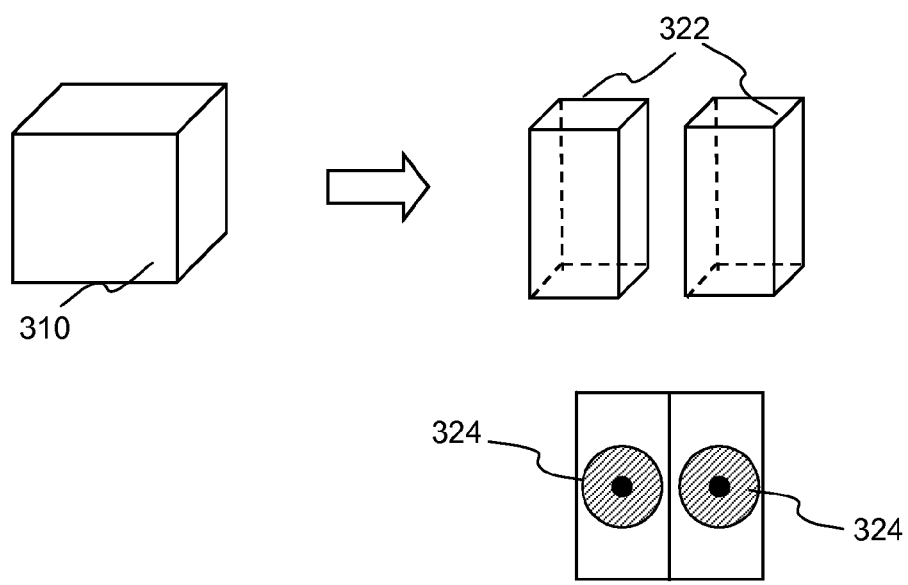
Figure 3C:
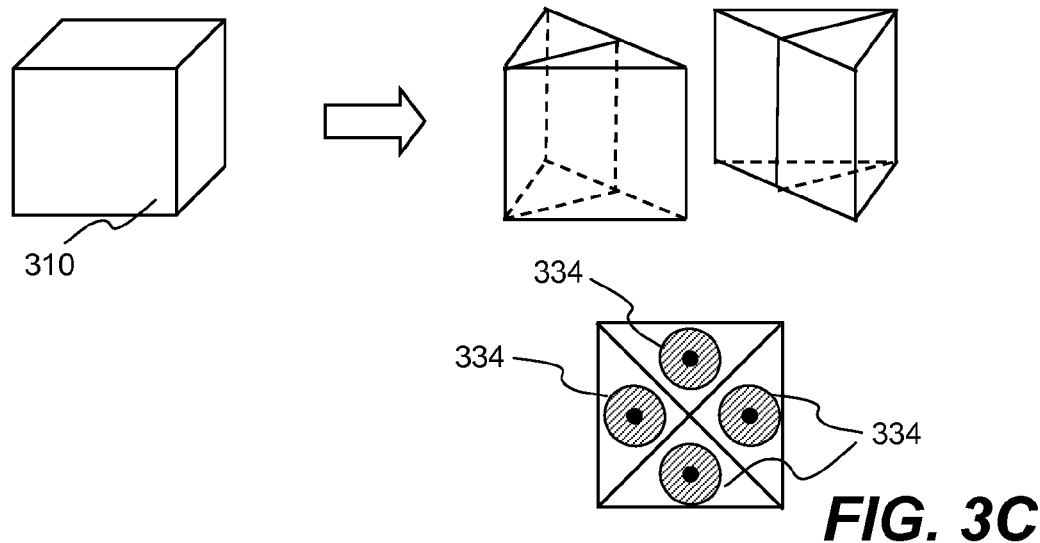
Figure 3D:
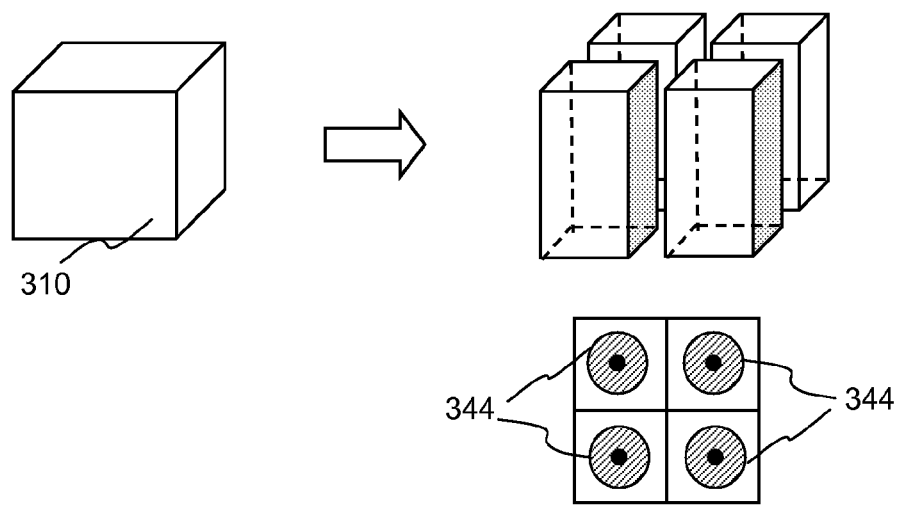
Figure 3E:
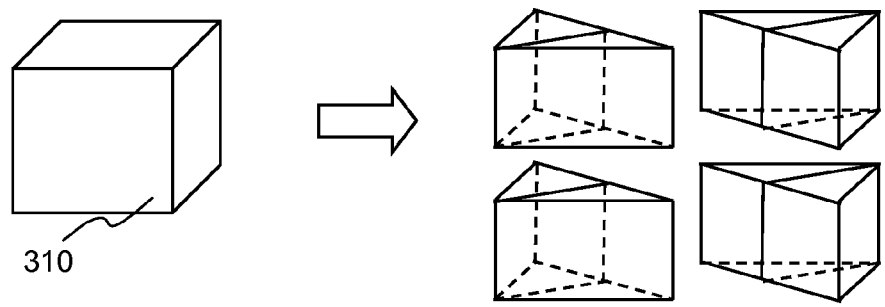
Figure 3F:
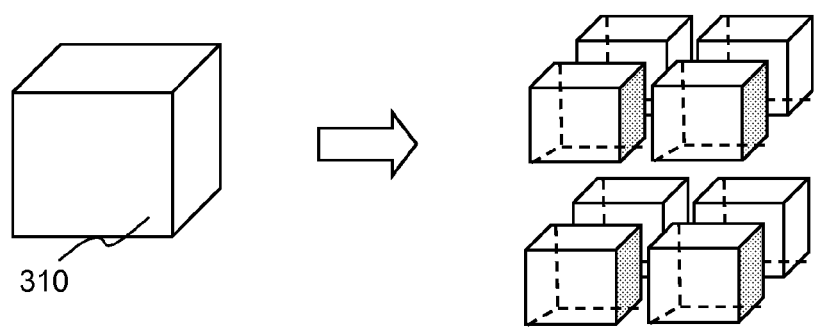
Figure 3G:
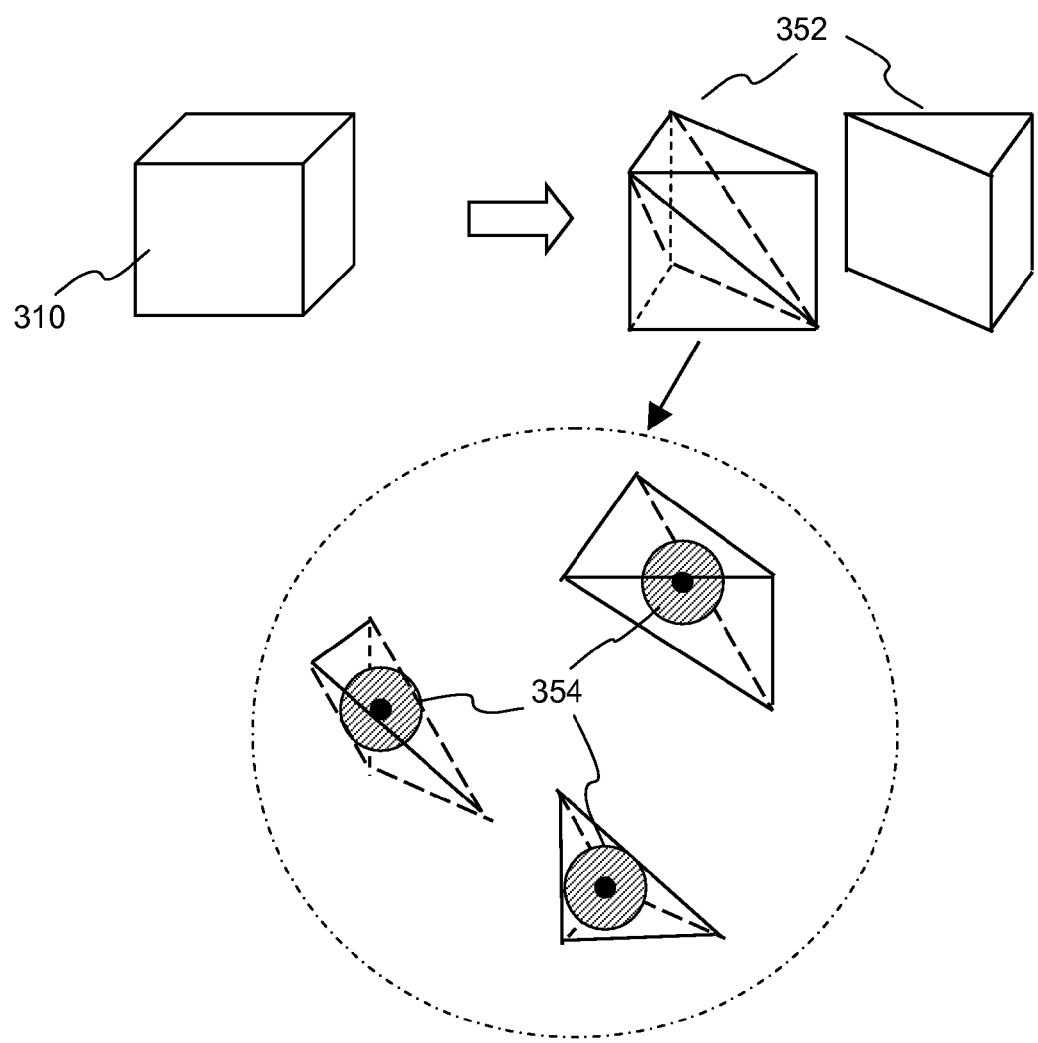

An alternative partition scheme shown in FIG. 3B, the failed element 310 is divided into two hexahedra 322, each of which is converted into a particle 324. According to other embodiments, the failed element 310 may also be converted into four particles 334-344 as shown in FIGS. 3C and 3D, or eight particles in FIGS. 3E and 3F. According to yet another embodiment shown in FIG. 3G, the failed element 310 is partitioned into six tetrahedra 352 that are then converted into six particles 354 (only three shown). It is noted that there is numerous possibilities for partitioning a single hexahedral element. Depending on the requirement of the engineering analysis, any one of the various partitioning schemes may be used. For example, simulating a shattered glass may require more particles to replace a failed element than simulating a bullet into a steel block. The partition schemes shown in FIGS. 3A-3G are referred to as adaptive smoothed particle hydrodynamics (SPH) schemes.

Figure 4A:
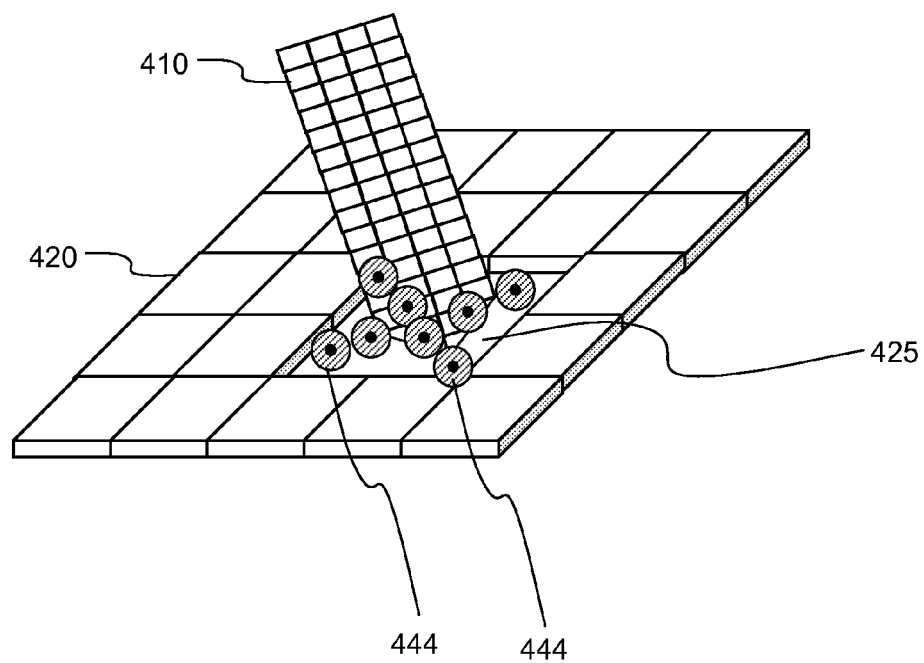
FIGS. 4A-4C are a sequence of diagrams illustrating the impact event using an exemplary hybrid approach with finite element method (FEM) and adaptive smoothed particle hydrodynamics (SPH), according to an embodiment of the present invention.
Figure 4B:
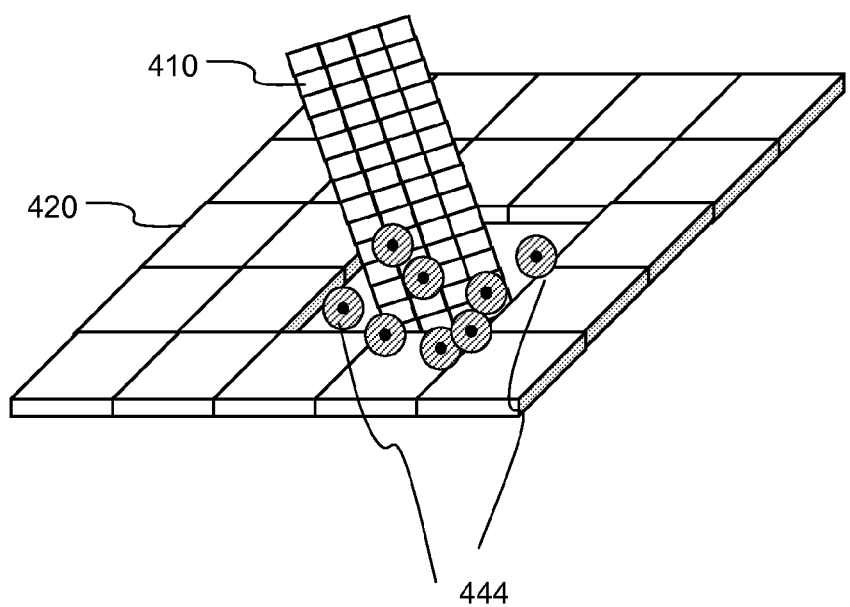
Figure 4C:
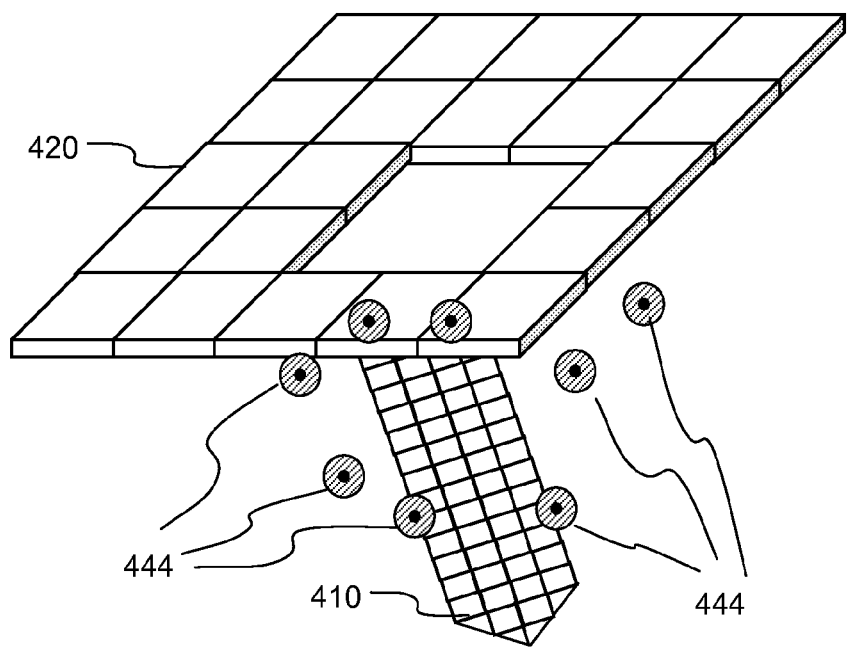

FIGS. 4A-4C are of diagrams illustrating the impact event (e.g., event shown FIGS. 1A-1C) using an exemplary hybrid approach with finite element method (FEM) and adaptive smoothed particle hydrodynamics (SPH), according to an embodiment of the present invention. FIG. 4A shows a projectile 410 is in contact with a structure 420, which is represented by a FEM grid model of 25 solid elements. To simulate a structural failure due to the impact, four 425 of the 25 elements in the contact area are replaced by eight particles 444, two particles per failed element. Each of the particles has a mass and velocity such that the principles of conservation of mass, momentum and energy are fulfilled. FIG. 4B and FIG. 4C show views of the impact event in later time.

Figure 5:
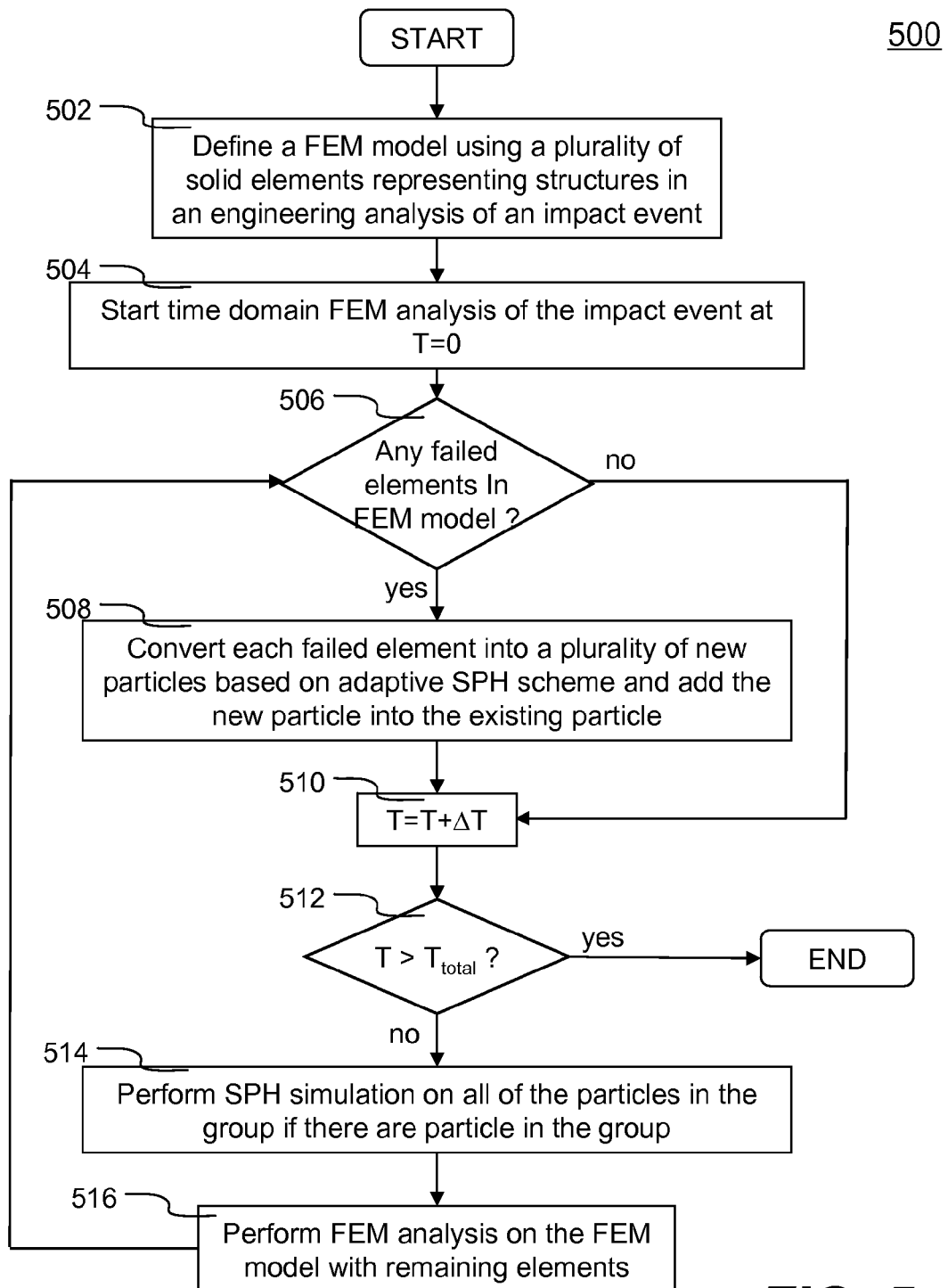
FIG. 5 is a flowchart illustrating an exemplary computer-implemented process of performing engineering analysis of an impact event using a hybrid approach of FEM and adaptive SPH, according to an embodiment of the present invention.

FIG. 5 is a flowchart illustrating an exemplary process 500 of performing engineering analysis of an impact event using a hybrid approach of FEM and adaptive SPH, according to an embodiment of the present invention. The process 500 may be implemented in software, hardware or a combination of both. The process 500 is preferably understood with previous figures.

The process 500 starts by defining a FEM model grid model using a plurality of solid finite elements (e.g., 8-node hexahedral elements) representing structures in a time domain simulation of engineering analysis of an impact event (e.g., the FEM model of the projectile 410 and the structure 420 in FIG. 4A) at 502. Next, at 504, the time domain simulation starts using FEM on the FEM grid model at the onset or time (T)=0. The process 500 then moves to a decision 506, in which it is determined whether there is any structural or material failure at current solution cycle. In one embodiment, the structural or material failure is checked element by element according to a constitutive equation defined in the FEM model. If 'yes', at 508, the process 500 converts each failed element into a plurality of particles based on one of the adaptive SPH schemes shown in FIG. 3A-3G and the newly converted particles are merged or added into a group of existed particles if any. Otherwise, if 'no', the process 500 skips step 508.

Next, at 510, the simulation time is incremented by a time increment or time step ΔT for the next solution cycle of the time domain simulation. The process 500 then determines whether the current time has reached the end of the time domain simulation, for example, the current time is checked against the total simulation time $T_{total}$ that is predefined. If 'no, the process 500, at 514, performs SPH calculations for the group of particles converted from the failed elements, if there is at least one particle in the group. Next the process 500 performs FEM analysis of the FEM grid model with remaining elements at 516. Then the process 500 moves back to decision 506 to repeat the steps described herein for each solution cycle until the decision 512 becomes 'yes'. The process 500 ends.

Figure 6:
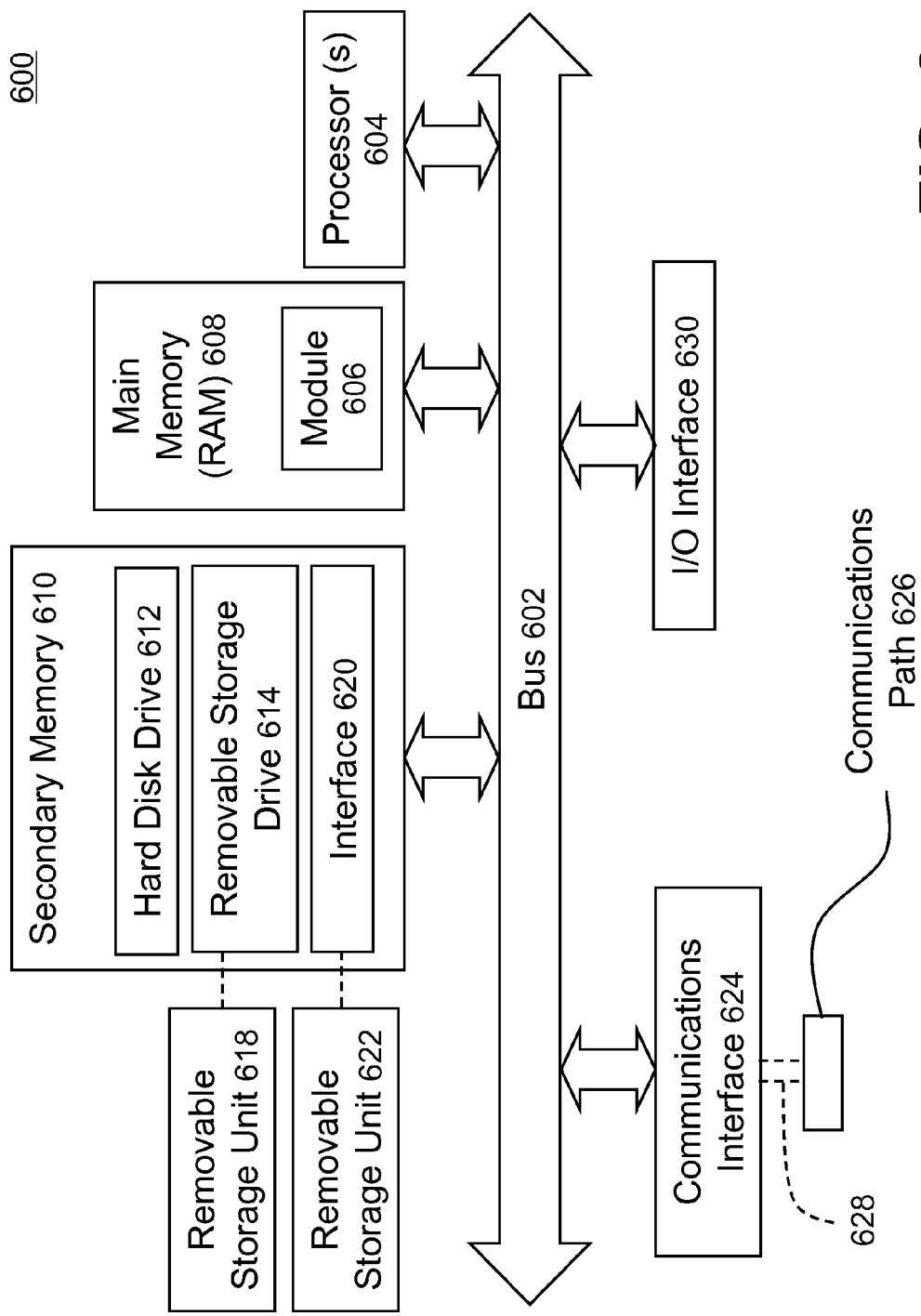
FIG. 6 is a function diagram showing salient components of a computing device, in which an embodiment of the present invention may be implemented.

According to one aspect, the present invention is directed towards one or more computer systems capable of carrying out the functionality described herein. An example of a computer system 600 is shown in FIG. 6. The computer system 600 includes one or more processors, such as processor 604. The processor 604 is connected to a computer system internal communication bus 602. Various software embodiments are described in terms of this exemplary computer system. After reading this description, it will become apparent to a person skilled in the relevant art(s) how to implement the invention using other computer systems and/or computer architectures.

Computer system 600 also includes a main memory 608, preferably random access memory (RAM), and may also include a secondary memory 610. The secondary memory 610 may include, for example, one or more hard disk drives 612 and/or one or more removable storage drives 614, representing a floppy disk drive, a magnetic tape drive, an optical disk drive, etc. The removable storage drive 614 reads from and/or writes to a removable storage unit 618 in a well-known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other similar means for allowing computer programs or other instructions to be loaded into computer system 600. Such means may include, for example, a removable storage unit 622 and an interface 620. Examples of such may include a program cartridge and cartridge interface (such as that found in video game devices), a removable memory chip (such as an Erasable Programmable Read-Only Memory (EPROM), Universal Serial Bus (USB) flash memory, or PROM) and associated socket, and other removable storage units 622 and interfaces 620 which allow software and data to be transferred from the removable storage unit 622 to computer system 600. In general, Computer system 600 is controlled and coordinated by operating system (OS) software, which performs tasks such as process scheduling, memory management, networking and I/O services. Exemplary OS includes Linux®, Microsoft Windows®.

There may also be a communications interface 624 connecting to the bus 602. Communications interface 624 allows software and data to be transferred between computer system 600 and external devices. Examples of communications interface 624 may include a modem, a network interface (such as an Ethernet card), a communications port, a Personal Computer Memory Card International Association (PCMCIA) slot and card, etc. Software and data transferred via communications interface 624 are in the form of signals 628 which may be electronic, electromagnetic, optical, or other signals capable of being received by communications interface 624. These signals 628 are provided to communications interface 624 via a communications path (i.e., channel) 626. This channel 626 carries signals (or data flows) 628 and may be implemented using wire or cable, fiber optics, a phone line, a cellular phone link, an RF link, a Bluetooth® wireless link and other communications channels.

The channel 626 facilitates a data flow 628 between a data network and the computer 600 and typically executes a special set of rules (i.e., a protocol) to send data back and forth. One of the common protocols is TCP/IP (Transmission Control Protocol/Internet Protocol) commonly used in the Internet. In general, the communication interface 624 manages the assembling of a data file into smaller packets that are transmitted over the data network or reassembles received packets into the original data file. In addition, the communication interface 624 handles the address part of each packet so that it gets to the right destination or intercepts packets destined for the computer 600.

In this document, the terms "computer program medium" and "computer usable medium" are used to generally refer to media such as removable storage drive 614, a hard disk installed in hard disk drive 612. These computer program products are means for providing software to computer system 600. The invention is directed to such computer program products.

The computer system 600 may also include an input/output (I/O) interface 630, which provides the computer system 600 to access monitor, keyboard, mouse, printer, scanner, plotter, and alike.

Computer programs (also called computer control logic) are stored as application modules 606 in main memory 608 and/or secondary memory 610. Computer programs may also be received via communications interface 624. Such computer programs, when executed, enable the computer system 600 to perform the features of the present invention as discussed herein. In particular, the computer programs, when executed, enable the processor 604 to perform features of the present invention. Accordingly, such computer programs represent controllers of the computer system 600.

In an embodiment where the invention is implemented using software, the software may be stored in a computer program product and loaded into computer system 600 using removable storage drive 614, hard drive 612, or communications interface 624. The application module 606, when executed by the processor 604, causes the processor 604 to perform the functions of the invention as described herein.

The main memory 608 may be loaded with one or more application modules 606 that can be executed by one or more processors 604 with or without a user input through the I/O interface 630 to achieve desired tasks. In operation, when at least one processor 604 executes one of the application modules 606, the results are computed and stored in the secondary memory 610 (i.e., hard disk drive 612). The status of the FEM analysis or SPH analysis is reported to the user via the I/O interface 630 either in a text or in a graphical representation.

In one embodiment, a first application module 606 is configured for performing the FEM analysis, while a second application module 606 for SHP analysis. A third application module 606 is configured for determining structural or material failure and for converting each failed element into a plurality of particles to be analyzed by SPH.

Although the present invention has been described with reference to be specific embodiments thereof, these embodiments are merely illustrative, and not restrictive, of, the present invention. Various modifications or changes to the specifically disclosed exemplary embodiments will be suggested to persons skilled in the art. For example, whereas the exemplary finite elements have been shown and described as 8-node solids or hexahedra, other types of elements such as pentahedra or heptahedra may be used. In summary, the scope of the invention should not be restricted to the specific exemplary embodiments disclosed herein, and all modifications that are readily suggested to those of ordinary skill in the art should be included within the spirit and purview of this application and scope of the appended claims.

What is claimed is:

1. A method executed in a computer system of conducting a time domain numerical simulation of an impact event using a hybrid approach of computer aided engineering analysis including finite element method (FEM) and adaptive smoothed particle hydrodynamics (SPH), said method comprising:
   (a) defining a plurality of FEM models each representing a structure in an impact event involving two or more structures, each of the FEM models having a plurality of finite elements;
   (b) conducting a time domain numerical simulation of the impact event using the FEM for the FEM models initially;
   (c) detecting and determining one or more failed finite elements in the FEM models based on a set of failure criteria;
   (d) dividing each of said one or more failed finite elements into a plurality of partitions, each partition being replaced by a SPH particle representing debris resulted from the impact event;
   (e) continuing the time domain numerical simulation using the FEM for the FEM models with remaining finite elements and using the adaptive SPH for said SPH particle and other SPH particles; and
   (f) repeating (c)-(e) until the time domain numerical simulation ends.

2. The method of claim 1, further comprises maintaining conservation of mass, momentum and energy between said each partition and said corresponding SPH particle.

3. The method of claim 2, wherein said mass, momentum and energy of said each partition are derived from said each of said one or more failed finite elements.

4. The method of claim 1, wherein said each of the plurality of partitions of a particular failed finite element has an equal size with one another.

5. The method of claim 1, wherein said each of the plurality of partitions for a particular failed finite element has a different size with one another.

6. The method of claim 1, wherein said SPH particle and said other SPH particles are configured for moving in a three-dimensional space without constraints.

7. The method of claim 1, wherein the set of failure criteria is derived from material properties and deformed configuration of each finite element in the FEM models.

8. The method of claim 1, further comprising forming a first group of particles for holding those SPH particles to be processed using the adaptive SPH.

9. The method of claim 8, further comprising forming a second group of particles for holding those SPH particles initially-converted from corresponding partitions of said each of said one or more failed finite elements.

10. The method of claim 1, wherein the time domain numerical simulation ends when a predefined total simulation time has reached.

11. The method of claim 1, wherein the plurality of finite elements comprises solid hexahedral finite elements.

12. A system for conducting a time domain numerical simulation of an impact event using a hybrid approach of computer aided engineering analysis including finite element method (FEM) and adaptive smoothed particle hydrodynamics (SPH), said system comprising:
   an input/output (I/O) interface;
   a memory for storing computer readable code for an application module;
   at least one processor coupled to the memory, said at least one processor executing the computer readable code in the memory to cause the application module to perform operations of:
   (a) defining a plurality of FEM models each representing a structure in an impact event involving two or more structures, each of the FEM models having a plurality of finite elements;
   (b) conducting a time domain numerical simulation of the impact event using the FEM for the FEM models initially;
   (c) detecting and determining one or more failed finite elements in the FEM models based on a set of failure criteria;
   (d) dividing each of said one or more failed finite elements into a plurality of partitions, each partition being replaced by a SPH particle representing debris resulted from the impact event;
   (e) continuing the time domain numerical simulation using the FEM for the FEM models with remaining finite elements and using the adaptive SPH for said SPH particle and other SPH particles; and
   (f) repeating (c)-(e) until the time domain numerical simulation ends.

13. The system of claim 12, further comprising forming a first group of particles for holding those SPH particles to be processed using the adaptive SPH and forming a second group of particles for holding those SPH particles initially-converted from corresponding partitions of said each of said one or more failed finite elements.

14. A computer usable non-transitory storage medium containing computer readable code for controlling a computer system for conducting a time domain numerical simulation of an impact event using a hybrid approach of computer aided engineering analysis including finite element method (FEM) and adaptive smoothed particle hydrodynamics (SPH) by a method comprising:
   (a) defining a plurality of FEM models each representing a structure in an impact event involving two or more structures, each of the FEM models having a plurality of finite elements;
   (b) conducting a time domain numerical simulation of the impact event using the FEM for the FEM models initially;
   (c) detecting and determining one or more failed finite elements in the FEM models based on a set of failure criteria;
   (d) dividing each of said one or more failed finite elements into a plurality of partitions, each partition being replaced by a SPH particle representing debris resulted from the impact event;
   (e) continuing the time domain numerical simulation using the FEM for the FEM models with remaining finite elements and using the adaptive SPH for said SPH particle and other SPH particles; and
   (f) repeating (c)-(e) until the time domain numerical simulation ends.

15. The computer usable non-transitory storage medium of claim 14, wherein said method further comprising forming a first group of particles for holding those SPH particles to be processed using the adaptive SPH and forming a second group of particles for holding those SPH particles initially-converted from corresponding partitions of said each of said one or more failed finite elements.

* * * * *